United States Patent
Hayden

(10) Patent No.: US 12,042,535 B2
(45) Date of Patent: Jul. 23, 2024

(54) METHODS TO PREPARE NASOPHARYNGEAL AND ORAL MATERIAL FOR ORAL INOCULATION OF COVID-19

(71) Applicant: Steven Mark Hayden, Las Vegas, NV (US)

(72) Inventor: Steven Mark Hayden, Las Vegas, NV (US)

( * ) Notice: Subject to any disclaimer, the term of this patent is extended or adjusted under 35 U.S.C. 154(b) by 352 days.

(21) Appl. No.: 17/223,920

(22) Filed: Apr. 6, 2021

(65) Prior Publication Data

US 2021/0315989 A1    Oct. 14, 2021

Related U.S. Application Data

(60) Provisional application No. 63/008,145, filed on Apr. 10, 2020.

(51) Int. Cl.
*A61K 39/215*    (2006.01)
*C12N 7/00*    (2006.01)
*A61K 39/00*    (2006.01)

(52) U.S. Cl.
CPC .............. *A61K 39/215* (2013.01); *C12N 7/00* (2013.01); *A61K 2039/53* (2013.01); *C12N 2770/20021* (2013.01); *C12N 2770/20022* (2013.01)

(58) Field of Classification Search
None
See application file for complete search history.

(56) References Cited

PUBLICATIONS

CWBio Product Sheet, Novel Coronavirus (SARS-CoV-2) Fast Nucleic Acid Detection Kit, May 21, 2020. (Year: 2020).*
Gouveia et al., J. Proteome Res., 2020, 19, 4407-4416. (Year: 2020).*
LaScola et al., European Journal of Clinical Microbiology & Infectious Diseases, 2020, 39:1059-1061. (Year: 2020).*
Malenovska, J Appl Microbiol., Dec. 2014; 117(6):1810-1819. (Year: 2014).*

* cited by examiner

*Primary Examiner* — Nicole Kinsey White

(57) ABSTRACT

The instant disclosure relates generally to oral inoculation and specifically to methods to prepare nasopharyngeal and oral material for oral inoculation of COVID-19. Severe acute respiratory syndrome coronavirus 2 ("SARS-CoV-2") viral particles are collected from at least one of a nasopharyngeal specimen and an oral specimen each derived from a patient infected with SARS-CoV-2 or a SARS-CoV-2 variant. Mammalian cells (e.g., Vero-E6 and/or Vero-CCL81 cells) are infected with the SARS-CoV-2 viral particles to produce infected mammalian cells. The infected mammalian cells are cultured to produce a mammalian cell culture. SARS-CoV-2 viral particles are collected from the mammalian cell culture to produce isolated viral particles. The isolated viral particles are frozen to produce a frozen isolate. The frozen isolate is partitioned into a plurality of tablets each having a therapeutically effective amount of the SARS-CoV-2 viral particles. An enteric coating is applied to each tablet.

15 Claims, 1 Drawing Sheet

```
┌─────────────────────────────────────────────────────────────┐
│ COLLECTING SEVERE ACUTE RESPIRATORY SYNDROME CORONAVIRUS 2  │
│ ("SARS-COV-2") VIRAL PARTICLES FROM AT LEAST ONE OF A       │──105
│ NASOPHARYNGEAL SPECIMEN AND AN ORAL SPECIMEN EACH DERIVED   │
│ FROM A PATIENT INFECTED WITH SARS-COV-2 OR A SARS-COV-2     │
│ VARIANT                                                     │
└─────────────────────────────────────────────────────────────┘
                              │
                              ▼
┌─────────────────────────────────────────────────────────────┐
│ INFECTING MAMMALIAN CELLS WITH THE SARS-COV-2 VIRAL         │──110
│ PARTICLES TO PRODUCE INFECTED MAMMALIAN CELLS               │
└─────────────────────────────────────────────────────────────┘
                              │
                              ▼
┌─────────────────────────────────────────────────────────────┐
│ CULTURING THE INFECTED MAMMALIAN CELL TO PRODUCE A          │──115
│ MAMMALIAN CELL CULTURE                                      │
└─────────────────────────────────────────────────────────────┘
                              │
                              ▼
┌─────────────────────────────────────────────────────────────┐
│ COLLECTING SARS-COV-2 VIRAL PARTICLES FROM THE MAMMALIAN    │──120
│ CELL CULTURE TO PRODUCE ISOLATED VIRAL PARTICLES            │
└─────────────────────────────────────────────────────────────┘
                              │
                              ▼
┌─────────────────────────────────────────────────────────────┐
│ FREEZING THE ISOLATED VIRAL PARTICLES TO PRODUCE A FROZEN   │──125
│ ISOLATE                                                     │
└─────────────────────────────────────────────────────────────┘
                              │
                              ▼
┌─────────────────────────────────────────────────────────────┐
│ PARTITION THE FROZEN ISOLATE INTO A PLURALITY OF TABLETS    │
│ EACH HAVING A THERAPEUTICALLY EFFECTIVE AMOUNT OF THE       │──130
│ SARS-COV-2 VIRAL PARTICLES                                  │
└─────────────────────────────────────────────────────────────┘
                              │
                              ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│     APPLYING AN ENTERIC COATING TO EACH TABLET              │──135
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

METHODS TO PREPARE NASOPHARYNGEAL AND ORAL MATERIAL FOR ORAL INOCULATION OF COVID-19

CROSS-REFERENCE TO RELATED APPLICATIONS

This application claims priority to U.S. Provisional Application No. 63/008,145 filed Apr. 10, 2020, which is hereby incorporated herein by reference.

FIELD OF THE INVENTION

The present disclosure relates generally to oral inoculation. More specifically, the present disclosure describes methods to prepare nasopharyngeal and oral material for oral inoculation of COVID-19.

BACKGROUND OF THE INVENTION

Current methods of reducing SARS-Co V-2 transmission include social distancing, wearing face masks, and vaccinations. However, it is becoming increasingly difficult to control SARS-CoV-2 respiratory spread. The working populations in many countries cannot afford N95 masks, expensive injections with unknown long-term side effects, nor economic and social isolation. The SARS-CoV-2 is currently reproducing in areas that are unable to control respiratory transmission, multiplication and mutation. As the transmissibility of respiratory mutants increases it become more difficult to control transmission. There exists a need in the art for solutions that address SARS-Co V-2 transmissions rates without resulting in serious side effects that are not burdensome on the economically distressed.

BRIEF DESCRIPTION OF THE DRAWINGS

Some of the embodiments will be described in detail, with reference to the following figures, wherein like designations denote like members, wherein:

FIGURE illustrates the process steps for a method to prepare material for oral inoculation of SARS-CoV-2 according to some embodiments.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, although steps of various processes or methods may be shown and described as being in a sequence or temporal order, the steps of any such processes or methods are not limited to being carried out in any sequence or order, absent an indication otherwise. Indeed, the steps in such processes or methods generally may be carried out in various sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. These headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

The present disclosure includes many aspects and features. Moreover, while many aspects and features relate to, and are described in the context of methods to prepare nasopharyngeal and oral material for oral inoculation of COVID-19, embodiments of the present disclosure are not limited to use only in this context.

Current methods of reducing SARS-Co V-2 transmission include social distancing, wearing face masks, and vaccinations. However, it is becoming increasingly difficult to control SARS-CoV-2 respiratory spread. The working populations in many countries cannot afford N95 masks, expensive injections with unknown long-term side effects, nor economic and social isolation. The SARS-CoV-2 is currently reproducing in areas that are unable to control respiratory transmission, multiplication and mutation. As the transmissibility of respiratory mutants increases it become more difficult to control transmission. There exists a need in the art for solutions that address SARS-Co V-2 transmissions rates without resulting in serious side effects that are not burdensome on the economically distressed.

Coronavirus infections historically are well tolerated causing only rhinitis and nasal congestion in billions of people. The entire coronavirus family infects the gastrointestinal tract usually with little or no symptoms. Coronavirus is very well tolerated in the intestines. SARS-CoV-2, a member of coronavirus family, produces a serious respiratory infection with severe symptoms. To be sure, SARS-CoV-2 only produces serious symptoms when it infects the pulmonary alveolus, which can result in serious disease and hospitalizations. If SARS-CoV-2 does not infect the alveolus there is no serious infection or disease. For example, if SARS-CoV-2 infects the intestinal tract, the result is limited to mild to moderate intestinal cramps and loose stool as opposed to fever chills, pneumonia, and sepsis. Prior to the coronavirus pandemic, coronavirus upper respiratory infections typically did not result in fevers, chills, or severe fatigue.

Avoiding alveolar infections avoids the systemic fever chills, fatigue, hospitalizations, and serious side effects. When SARS-CoV-2 infects the pulmonary alveolus, it multiplies into many millions of virus particles in asymptomatic phase. Eventually the alveolus fills with many millions of virus particles that cause viral sepsis in the blood stream. Alveolar multiplication is necessary to create fever chills, pulmonary and other systemic complications.

Not to be limited by theory, if intestinal exposure of SARS-CoV-2 can occur without alveolar infection, then there would be no systemic side effects of fever chills and fatigue. It is also theorized that intestinal exposure can create an alveolar defense that would stop airborne transmission of virus. Thus, if the SARS-CoV-2 virus does not multiply on the alveolus, it cannot spread through the air and be transmitted. Despite millions of intestinal infections, there are almost no cases of stool to respiratory transmission. Accidental intestinal exposure occurs secondary to oral live virus being swallowed from mouth via accidental exposure. The vast majority of live oral SARS-CoV-2 is killed by stomach acid. However, often a few viruses will make it to the small intestine and establish an intestinal infection of SARS-CoV-2.

Intestinal exposure of SARS-CoV-2 results in an intestinal infection of SARS-CoV-2. When the SARS-CoV-2 intestinal infection occurs without alveolar infection there are only mild gastrointestinal ("GI") side effects and no fever chills and myalgia. SARS-CoV-2 severely depressed the world economy. Most nations responded in a traditional manner to the COVID epidemic. Many nations funded research in intramuscular vaccines, but COVID is not a traditional respiratory infection. SARS-CoV-2 spreads mostly in the asymptomatic phase and is based on multiplication at the alveolus. Speaking, singing, or making noise in the chest vibrates the alveolus and aerosolizes the virus thereby making transmittable to others.

Traditional intramuscular vaccines are injected into the muscle and create elevated serum antibodies. These serum antibodies are typically considered proof of intramuscular vaccine effectiveness. However, serum antibodies are not effective unless they impact the multiplication of the virus in the alveolus, which means that intramuscular vaccines cannot completely eliminate the transmission of virus from the alveolus. On the other hand, intestinal infection of SARS-CoV-2 enhances alveolar defense and reduces transmission at a higher rate compared to intramuscular vaccines.

Since the arrival of SARS-CoV-2 in 2019, the virus continues to mutate thereby increasing the chance of the development of increasingly transmissible strains. For example, the virus may acquire more capacitance to increase its electrostatic charge and facilitate its escape from the same charged alveolus. Alternatively, the virus may increase its viral replication rates in the alveolus. It is true that replications in the intestines allow mutations to occur, but intestinal mutants are not spread from the intestinal tract. Reported cases of fecal spreading are rare and SARS-CoV-2 dies in the sewage system. Hence, it is safe to conclude that intestinal mutants do not promote spread of SARS-CoV-2 respiratory disease. Stool mutations die and do not lead to respiratory mutants that multiply faster or aerosolize better.

Vaxart, Inc. is an intestinal oral vaccine company that promotes oral vaccines that are based on adenovirus vector. The oral inoculation method disclosed in the instant disclosure does not use adenovirus as a vector, which distinguishes the oral live SARS-CoV-2 vaccine from vector-based oral vaccines such as disclosed by Vaxart, Inc. Vaxart Covid vaccine uses genetic code for the spike protein that is installed in adenovirus. Vaxart has never utilized coronavirus as a vector or to our knowledge even experimented with coronavirus as a vector. The safety and efficacy of one viral family as a vector does not apply across viral families.

Oral live SARS-CoV-2 result in improved alveolar defense with no significant alveolar multiplication transmission ten days after the successful intestinal infection. This occurs accidentally when naturally infected individuals receive an accidental intestinal exposure and are unable to transmit the virus ten days after intestinal exposure. Inoculation uses deliberate intentional intestinal exposure to create an intestinal infection of coronavirus that can last for weeks. This exposure allows long lasting IgA antibodies to be formed for long term defense of the alveolar surface. It is alveolar SARS-CoV-2 growth that allow for respiratory spread of the virus.

It is believed that vector-based oral vaccines fail because the adenovirus does not colonize the intestinal tract as well as SARS-CoV-2. Typically, SARS-CoV-2 remains in the intestines for up to weeks at a time and allows for the best possible antibody to antigen matching by the intestinal immune defense. Extended intestinal growth of adenovirus (e.g., up to several weeks) has not yet been established. The SARS-CoV-2 intestinal growth can be monitored by PCR and rapid antigen testing of the stool. Frequently, SARS-CoV-2 typically grows for weeks in the intestines without systemic side effects. A single active intestinal infection of SARS-Cov-2 produces 99.5 percent or more prevention of transmission. In contrast, adenovirus vector-based vaccines have not been shown to produce the same reduction in transmission.

Traditional vaccines have been developed to stop the spread of SARS-Cov-2. Aerosol transmission of SARS typically does not occur from exposure to the bloodstream. Serum antibody levels have reduced influence on viral replication that occurs on the surface of the alveolus. Current data reflects that intramuscular vaccines are only ninety (90) percent or less effective at reducing air spread of SARS-CoV-2 even when combines with best N95 masking techniques. However, intestinal SARS-CoV-2 infection typically reduces 99.5 percent or more of all respiratory transmission within ten days. This means that intestinal infection promotes reduction of alveolar multiplication of SARS-CoV-2.

Intramuscular vaccines create fever chills and local soreness in a substantial portion of the vaccinated. Intestinal exposure to SARS-CoV-2 typically creates mild gastric cramps and loose stool. Local population can disapprove of the side effects of the intramuscular vaccines and refuse vaccination. In undeveloped countries, 95 percent of the population will not typically consent to COVID vaccinations that have undesirable side effects. Unless immunization reaches 90-95 percent, the virus will continue to spread and mutate in undeveloped countries and become more transmissible and resistant to treatment.

Obviously, such mutants have developed and will continue to develop. Individuals can receive multiple doses of an intramuscular SARS-CoV-2 vaccine, which mimic a pathogenic viral attack in the bloodstream and causes fever, chills, and fatigue. Repeated immunization of intramuscular vaccines cause hypersensitivity to develop as symptoms progressively become more severe with each repeated intramuscular dose. As a result, the incidence of severe complications and side effects goes up with the number of intramuscular SARS-CoV-2 dosages a subject receives. None of current intramuscular vaccines for SARS-CoV-2 have more than 2 doses.

However, intestinal inoculation of SARS-CoV-2 desensitizes the person to SARS-CoV-2 where each intestinal exposure produces less symptoms not more symptoms. Intestinal inoculation reduces symptoms with each subsequent dose. Hence, a patient can expose themselves daily to intestinal SARS-CoV-2 for the remainder of their life with minimal symptoms. However, daily injections of SARS-CoV-2 vaccine injections would sensitize an individual and create extreme serious progressively harmful immune symptoms that would become intolerable and disabling if not fatal. SARS-CoV-2 is likely to be present and mutate for several years, which requires the development of long-term immune therapies that can address viral mutations and be administered on a frequent basis.

The instant disclosure seeks to provide a method for oral inoculation of SARS-CoV-2. FIG. 1 depicts the process steps of a method to prepare material for oral inoculation of SARS-CoV-2. At Step 105, SARS-CoV-2 viral particles are collected from at least one of a nasopharyngeal specimen and an oral specimen each derived from a patient infected with SARS-CoV-2 or a SARS-CoV-2 variant. At Step 110, mammalian cells are infected with the SARS-CoV-2 viral particles to produce infected mammalian cells. For example, applicable mammalian cells include, but are not limited to, Vero cells (e.g., Vero-E6 cells and Vero-CCL81). At Step 115, the infected mammalian cells are cultured to produce a mammalian cell culture. At Step 120, SARS-CoV-2 viral particles are collected from the mammalian cell culture to produce isolated viral particles.

In preferred embodiments, SARS-CoV-2 viral particles are collected from the mammalian cell culture when the mammalian cell culture have about 1,000 to 10,000,000 viable SARS-CoV-2. At Step 125, the isolated viral particles are collected to produce a frozen isolate. In preferred embodiments, the isolated vial particles mixed with gelatin (e.g., up to 10 wt %) to produce a solution, which is frozen to produce the frozen isolate. To be sure, other stabilizers that are similar to gelatin are applicable. At Step 130, the frozen isolate is partitioned into a plurality of tablets each having a therapeutically effective amount of the SARS-CoV-2 viral particles. The tablets can be coated. An enteric coating is a barrier that controls the location of oral medication in the digestive system where it is absorbed. The word "enteric" indicates small intestine; therefore, enteric coatings prevent release of medication before it reaches the small intestine. The enteric coated polymers remain stable at low pH, and therefore remain insoluble. But as the pH increases in the gastrointestinal tract, the acidic functional groups are capable of ionization, and the polymer (coating) swells or becomes soluble in the intestinal fluid. In certain embodiments, the method further includes Step 135, where an enteric coating is applied to each tablet. Applicable enteric coatings include but are not limited to cellulose acetate phthalate, cellulose acetate trimellitate, poly(vinyl acetate phthalate), hydroxypropyl methylcellulose phthalate, fatty acids, waxes, shellac, plastics, and/or plant fibers.

Alternative intestinal inoculation methods are also available. For example, the rectal mucosa contains ACE2 receptors that are used for cellular attachment and entry by the COVID-19 virus. Therefore, vaccine suppository is possible. For example, stool samples are often positive for COVID-19. COVID positive stool samples of 100 gram each were collected from ten donors that are positive for COVID-19. The samples from ten donors were gently mixed and constitute 10,000 grams of stool and likely contain billions of dead and live COVID-19 virus particles. The mixture was gently blended and frozen with 10 wt % glycerol and frozen into 10,000 one milliliter stool suppositories. During administration, recipients should be closely evaluated and managed. One rectal suppository should be administered daily for the first three days, and stopped if diarrhea, fever, or complications occur. Antibody tests should be done on subjects before and after testing to confirm immunity.

The live virus in the intestines will not magically make it to the pneumocytes. Under all ordinary circumstances, stool that contains SARS-CoV-2 is flushed into toilet and not placed in a nebulizer to be inhaled.

It is pulmonary COVID-19 complications that will disable with ARDS. The IgA made by the gut can protect the bronchial epithelium. Minimize rectal inflammation and through a small inoculation over a small area with live viruses. Smaller inoculation is better since less tissue is at risk of inflammation. A large enema might expose a large area to inflammation and disease. The inflammatory reaction may be unexpectedly strong, which is why a small dose of 1 ml suppository is initially used and gradually increased in frequency and dosage. The rectum is physically resilient organ. Rectal perforations are very rare even with mild to moderate rectal trauma during anal intercourse. The viral rectal dose should start small and increase until immunity occurs. Those sick with COVID pneumonia may benefit from frozen rectal suppositories as well after testing them for safety. A hundred stools from ten patients may treat hundreds if not thousands of patients in the simple rectal suppository. Eventually, the virus may be cultured for pure virus without any risk of other fecal contaminants. Eventually, in a year or two, a true classic live virus of known potency may use a rectal application with a known precise amount of live or dead virus. Diarrhea is expected as the most likely symptom, but it can be treated with IV fluids if the subject becomes dehydrated.

When members of the community are accidentally infected in the respiratory tract, their alveolar immunity benefits if the SARS-CoV-2 to reaches their small intestine as rapidly as possible. Infected individual with SARS-CoV-2 is already swallowing the saliva in the mouth that contains live virus. However, most of the accidentally swallowed virus is killed by stomach acid. They can put their own saliva in an enteric capsule and swallow it to prevent acid destruction. In this way more live SARS-CoV-2 virus will reach the small intestine faster to mount an immune response. The research director should swallow saliva from SARS-CoV-2 positive patients to demonstrate that the process is safe. Due to the risk of cytomegalovirus and herpes family in the donor the donors should be screened for mouth sores or presence of other viruses or bacteria. It is recommended that research director take acyclovir to reduce risk of herpes family virus when consuming saliva samples from other donors.

Although the disclosure has been explained in relation to its preferred embodiment, it is to be understood that many other possible modifications and variations can be made without departing from the spirit and scope of the disclosure.

What is claimed is:

1. A method to prepare material for oral inoculation of SARS-CoV-2 comprising:
   collecting severe acute respiratory syndrome coronavirus 2 ("SARS-CoV-2") viral particles from at least one of a nasopharyngeal specimen and an oral specimen each derived from a patient infected with SARS-CoV-2 or a SARS-CoV-2 variant;
   infecting mammalian cells with the SARS-CoV-2 viral particles to produce infected mammalian cells;
   culturing the infected mammalian cell to produce a mammalian cell culture;
   collectingSARS-CoV-2 viral particles from the mammalian cell culture to produce isolated viral particles;
   freezing the isolated viral particles to produce a frozen isolate;
   partition the frozen isolate into a plurality of tablets each having a therapeutically effective amount of the SARS-CoV-2 viral particles; and
   applying an enteric coating to each tablet.

2. The method of claim 1, wherein
   infecting the mammalian cells with the SARS-CoV-2 viral particles comprises infecting Vero cells with the SARS-CoV-2 viral particles.

3. The method of claim 2, wherein
   Collecting SARS-CoV-2 viral particles from the mammalian cell culture comprises:
      collecting SARS-CoV-2 viral particles from the mammalian cell culture when the mammalian cell culture comprises 1,000 to 10,000,000 viable SARS-CoV-2.

4. The method of claim 3, wherein
   freezing the isolated viral particles comprises:
      mixing the isolated vial particles with gelatin to produce a solution; and
      freezing the solution to produce the frozen isolate.

5. The method of claim 4, wherein
   mixing the isolated vial particles with gelatin comprises:
      mixing the isolated vial particles with 10 wt % gelatin.

6. The method of claim 5, wherein
   the enteric coating comprises one or more of:
      cellulose acetate phthalate;
      cellulose acetate trimellitate;
      poly(vinyl acetate phthalate);
      hydroxypropyl methylcellulose phthalate;
      fatty acids;
      a wax;
      shellac;
      a plastic; and
      a plant fiber.

7. The method of claim 6, wherein
   the Vero cells comprise Vero-E6 cells.

8. A method to prepare material for oral inoculation of SARS-CoV-2 comprising:
   collecting acute respiratory syndrome coronavirus 2 ("SARS-CoV-2") viral particles from at least one of a nasopharyngeal specimen and an oral specimen each derived from a patient infected with SARS-CoV-2 or a SARS-CoV-2 variant;
   infecting mammalian cells with the SARS-CoV-2 viral particles to produce infected mammalian cells, the mammalian cells comprise Vero cells;
   culturing the infected mammalian cell to produce a mammalian cell culture;
   collecting SARS-CoV-2 viral particles from the mammalian cell culture to produce isolated viral particles;
   freezing the isolated viral particles to produce a frozen isolate;
   partition the frozen isolate into a plurality of tablets each having a therapeutically effective amount of the SARS-CoV-2 viral particles; and
   applying an enteric coating to each tablet.

9. The method of claim 8, wherein
   the Vero cells comprise Vero-E6 cells.

10. The method of claim 8, wherein
    collecting SARS-CoV-2 viral particles from the mammalian cell culture comprises:
       collecting SARS-CoV-2 viral particles from the mammalian cell culture when the mammalian cell culture comprises 1,000 to 10,000,000 viable SARS-CoV-2.

11. The method of claim 8, wherein
    freezing the isolated viral particles comprises:
       mixing the isolated vial particles with gelatin to produce a solution; and
       freezing the solution to produce the frozen isolate.

12. The method of claim 11, wherein
    mixing the isolated vial particles with gelatin comprises:
       mixing the isolated vial particles with 10 wt % gelatin.

13. The method of claim 12, wherein
    the enteric coating comprises one or more of:
       cellulose acetate phthalate;
       cellulose acetate trimellitate;
       poly(vinyl acetate phthalate);
       hydroxypropyl methylcellulose phthalate;
       fatty acids;
       a wax;
       shellac;
       a plastic; and
       a plant fiber.

14. A method to prepare material for oral inoculation of SARS-CoV-2, the method comprising:
    collecting severe acute respiratory syndrome coronavirus 2 ("SARS-CoV-2") from at least one of a nasopharyngeal specimen and an oral specimen each derived from a patient infected with SARS-CoV-2 or a SARS-CoV-2 variant;
    infecting mammalian cells with the SARS-CoV-2 viral particles to produce infected mammalian cells;
    culturing the infected mammalian cell to produce a mammalian cell culture;

collecting SARS-CoV-2 viral particles from the mammalian cell culture when the mammalian cell culture comprises 1,000 to 10,000,000 viable SARS-CoV-2 to produce isolated viral particles;

mixing the isolated vial particles with gelatin to produce a solution;

freezing the solution to produce a frozen isolate;

partition the frozen isolate into a plurality of tablets each having a therapeutically effective amount of the SARS-CoV-2 viral particles; and applying an enteric coating to each tablet.

15. The method of claim 14, wherein the mammalian cells comprise one or more Vero-E6 cells.

* * * * *